United States Patent [19]

Aardse

[11] 4,376,628

[45] Mar. 15, 1983

[54] DEVICE FOR TREATING TEETH

[75] Inventor: Henri J. Aardse, Hilversum, Netherlands

[73] Assignee: B.V. Gaba, Hilversum, Netherlands

[21] Appl. No.: 230,948

[22] PCT Filed: May 9, 1980

[86] PCT No.: PCT/NL80/00016

§ 371 Date: Jan. 9, 1981

§ 102(e) Date: Jan. 9, 1981

[87] PCT Pub. No.: WO80/02368

PCT Pub. Date: Nov. 13, 1980

[30] Foreign Application Priority Data

May 9, 1979 [NL] Netherlands ............... 7903648

[51] Int. Cl.³ .............................................. A61C 17/02
[52] U.S. Cl. ..................................... 433/80; 433/42;
433/217; 178/136
[58] Field of Search .................... 433/80, 42, 217;
128/176, 136, 134, 260

[56] References Cited

U.S. PATENT DOCUMENTS

| Re. 28,667 | 12/1975 | Gores ............................. 433/42 |
| 1,146,264 | 7/1915 | Kelly ............................. 128/136 |
| 2,857,909 | 10/1958 | Johnson ......................... 128/136 |
| 4,173,219 | 11/1979 | Lantiue et al. ................ 128/136 |

*Primary Examiner*—Robert Peshock
*Attorney, Agent, or Firm*—Scully, Scott, Murphy & Presser

[57] ABSTRACT

A device for treating teeth with a tooth treating medium, such as a fluorine-containing agent, in which two U-shaped trough members are formed of a soft synthetic plastic. One of the trough members is designed to be applied about the upper teeth and the other about the lower teeth. The upper and lower trough members are interconnected at their bottom by a single centrally located connector element. A forwardly projecting handle on the connector element enables the device to be hygenically handled. The two U-shaped members are centered relative to each other by two sets of intermeshing ridges thereon.

5 Claims, 4 Drawing Figures

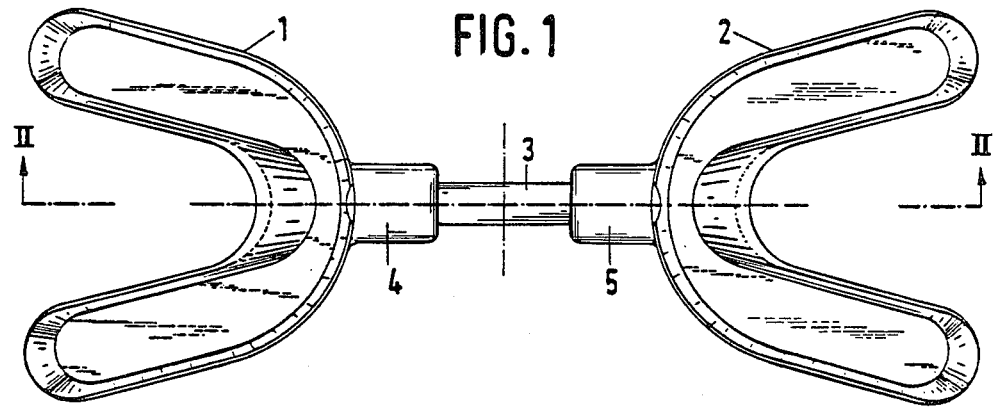
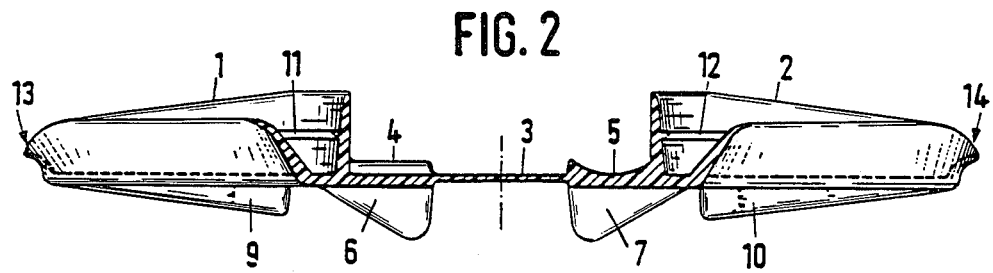
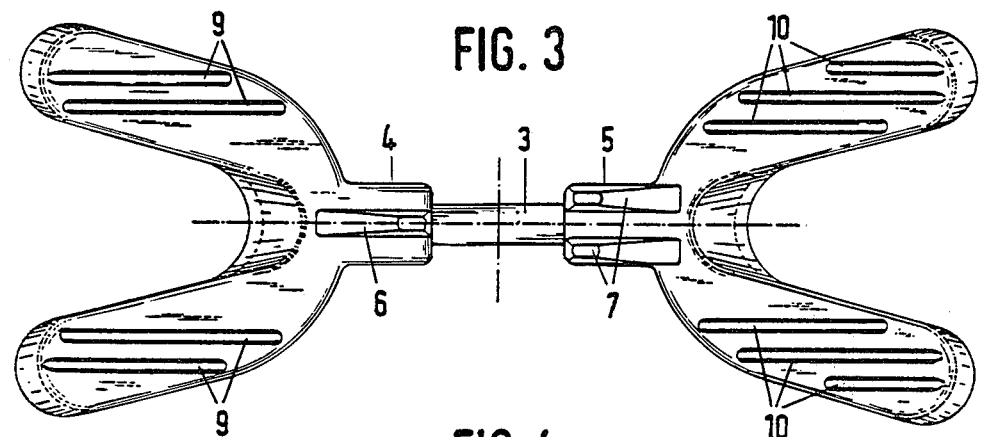
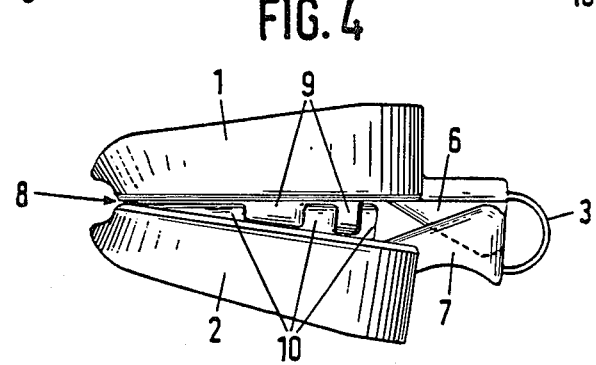

DEVICE FOR TREATING TEETH

This invention relates to a device for treating teeth with a tooth treating medium, such as a fluorine-containing agent.

A prior device, disclosed in Dutch patent application No. 77,09035, comprises two trough members, substantially U-shaped, and made of soft synthetic plastics material, one of said members being designed to be applied about the upper teeth, and the other about the lower teeth, said members being interconnected by at least one flexible connector. In this prior device, the trough members have the ends of their legs interconnected by flexible connectors, and are further provided at the outside of the bottom with gripping lips for the device to be introduced into a patient's mouth cavity. Furthermore, the trough members are provided on the outside with teeth by means of which they can be held in a fixed operative position relative to each other.

It is an object of the present invention to improve this prior device.

For this purpose, according to the invention, there is provided a device for treating teeth with a tooth treating medium, such as a fluorine-containing agent, comprising two substantially U-shaped trough members made of soft synthetic plastics material, one of said trough members being designed to be applied about the upper teeth and the other about the lower teeth, said members being interconnected by at least one flexible connector, characterized in that the two U-shaped members are interconnected by a single connector lip, provided in the plane of symmetry of each of the two members and connecting with said members at the trough bottoms. This connector lip can be made with a sufficient length and surface area for the device to be easily and hygienically handled by the operator. Furthermore, by virtue of there being no connectors at the ends of the U-shaped members, unnecessary irritation of the mouth is avoided.

In a further elaboration of the invention, the connector lip is provided with means for centering the two U-shaped members relatively to each other, so that the device may be properly placed in the mouth. In one embodiment, the centering means take the form of co-acting centering ridges extending in a direction parallel to said plane of symmetry, each of said ridges being bevelled in the direction of the adjacent U-shaped member. It is thus achieved that the free ends of the legs of the U-shaped members can be pressed towards each other, and the device can be easily placed in the mouth. This is in contrast to the prior device, where the free ends of the legs of the U-shaped members are apart.

In another embodiment, the bottoms of the legs of the U-shaped members are provided on the outside with co-acting ridges extending in a direction parallel to said plane of symmetry. This provides for further centering in a direction perpendicular to said plane of symmetry, while the U-shaped members can move in a direction parallel to said plane of symmetry, which makes for better adaptation to a set of teeth with prominent front teeth.

In order to facilitate the introduction of the device and its being kept in the mouth for some time, the ridges provided on the legs of the U-shaped members may each be bevelled towards the ends of the legs.

In a further elaboration of the invention, in order to provide for flexible, non-irritating connection to the gums the wall thickness of the U-shaped members decreases towards the edge destined for connection with the gums.

Preferably the U-shaped members are each provided on the inside of the trough with at least one edge for supporting an inlay element. Such an inlay element may be used, for example, if the device is too large for the set of teeth to be treated, but also if a thin-liquid tooth treating agent must be used.

One embodiment of the invention will now be described with reference to the accompanying drawings, in which:

FIG. 1 shows a bottom view of a device for treating teeth according to the present invention;

FIG. 2 shows a cross-sectional view, taken on the line II—II of FIG. 1;

FIG. 3 is a bottom view of the device shown in FIGS. 1 and 2; and

FIG. 4 is a side-elevation of view of the device of FIGS. 1–3 in the position ready for use.

Referring to the drawings, there is shown a device for treating a set of teeth, comprising a pair of substantially U-shaped trough members 1 and 2, made of soft synthetic plastics material, which members are interconnected by a flexible connector lip 3. This connector lip connects with the two trough members 1 and 2 at the position of their plane of symmetry, and this at the level of the bottom of each trough.

As shown, the connector lip has broadened portions 4 and 5 at the places where it connects with the trough members. Formed on these broadened portions, centering lugs 6 and 7, respectively, are provided on the side away from the open side of the trough, which lugs centre the two trough members 1 and 2 relatively to each other when the device is moved into the operative position shown in FIG. 4. As further shown, the centering lugs are bevelled so that when pressure is exerted on the trough member in the operative position of the device the two trough members are forced towards each other (FIG. 4), as a result of which the ends of the legs (see the point designated 8 in FIG. 4) are in proper contact with each other.

The bottoms of the legs of the U-shaped members 1 and 2 are provided on the outside with co-acting centering ridges 9 and 10, respectively, extending in a direction parallel to the plane of symmetry referred to. As shown in FIGS. 2 and 4, these centering ridges are bevelled in the same direction as are lugs 6 and 7. Centering ridges 9 and 10 permit a movement of the U-shaped members in a direction parallel to the plane of symmetry referred to, but not in a direction at right angles thereto: as a result the device can be used without any problems in case there is an overbite or underbite.

As shown in FIG. 2, the U-shaped members are provided on the inside of the trough with an edge 11, 12, respectively, by means of which an inlay element not shown can be supported. These edges 11 and 12 have been omitted from FIG. 1 for clarity.

As further shown in the drawings, the wall thickness of the U-shaped members decreases towards the free edge. Furthermore, the trough is of reduced height at the free end of each leg (FIG. 2, the places designated 13 and 14, respectively). This makes for proper connection of the device to the gums without on the other hand causing irritation.

Finally it is noted that a large number of modifications and alteration are possible without departing from the scope of the invention. Thus, for example, the connector lip may be provided with a weakened portion to enable the U-shaped members to be readily separated, should this be desired.

I claim:

1. A device for treating teeth with a tooth treating medium, such as a fluorine-containing agent, comprising two substantially U-shaped trough members made of soft synthetic plastics material, one of said trough members being designed to be applied about the upper teeth and the other about the lower teeth, said members being interconnected by at least one flexible connector, characterized in that the two U-shaped members are interconnected by a single centrally located projecting connector element, provided centrally in the plane of symmetry of each of the two members and connecting with said members at the trough bottoms with the centrally located single connector element projecting forwardly from the mouth when said two trough members are positioned to be placed on the teeth to provide a forwardly projecting handle to enable the device to be hygenically handled by the operator without entering the cavity of the mouth, said connector element being provided with means for centering the two U-shaped members relatively to each other, including two sets of centering ridges extending in a direction parallel to said plane of symmetry with the two sets of ridges intermeshing when said two trough members are positioned to be placed on the teeth, each of said ridges being bevelled in the direction of the adjacent U-shaped members.

2. A device as claimed in claim 1, wherein the bottoms of the legs of the U-shaped members are provided on the outside with intermeshing ridges extending in a direction parallel to said plane of symmetry.

3. A device as claimed in claim 2 wherein the ridges provided on the legs of the U-shaped members are each bevelled towards the ends of the legs.

4. A device as claimed in claims 1, 2 or 3, wherein the wall thickness of the U-shaped members decreases towards the edge destined for connection with the gums.

5. A device as claimed in claims 1, 2, or 3, wherein the U-shaped members are each provided on the inside of the trough with at least one edge for supporting an inlay element.

* * * * *